US009254307B2

(12) United States Patent
Dunn et al.

(10) Patent No.: US 9,254,307 B2
(45) Date of Patent: *Feb. 9, 2016

(54) POLYMERIC DELIVERY FORMULATIONS OF LEUPROLIDE WITH IMPROVED EFFICACY

(75) Inventors: Richard L. Dunn, Fort Collins, CO (US); John Steven Garrett, Fort Collins, CO (US); Harish Ravivarapu, Union City, CA (US); Bhagya L. Chandrashekar, Fort Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/784,343

(22) Filed: May 20, 2010

(65) Prior Publication Data

US 2010/0234305 A1    Sep. 16, 2010

Related U.S. Application Data

(63) Continuation of application No. 11/643,505, filed on Dec. 21, 2006, now abandoned, which is a continuation of application No. 10/872,671, filed on Jun. 21, 2004, now abandoned, which is a continuation of application No. 10/373,400, filed on Feb. 24, 2003, now Pat. No. 6,773,714, which is a continuation of application No. 09/711,758, filed on Nov. 13, 2000, now Pat. No. 6,565,874, and a continuation-in-part of application No. 09/666,174, filed on Sep. 21, 2000, now abandoned, which is a continuation-in-part of application No. 09/643,289, filed on Aug. 22, 2000, now Pat. No. 6,630,155, which is a continuation of application No. 09/181,355, filed on Oct. 28, 1998, now Pat. No. 6,143,314.

(51) Int. Cl.
| | |
|---|---|
| *A61K 38/09* | (2006.01) |
| *A61K 9/00* | (2006.01) |
| *A61K 9/19* | (2006.01) |
| *A61K 47/34* | (2006.01) |
| *A61K 47/22* | (2006.01) |
| *B65D 81/32* | (2006.01) |

(52) U.S. Cl.
CPC ............... *A61K 38/09* (2013.01); *A61K 9/0024* (2013.01); *A61K 9/19* (2013.01); *A61K 47/22* (2013.01); *A61K 47/34* (2013.01); *B65D 81/3205* (2013.01)

(58) Field of Classification Search
CPC combination set(s) only.
See application file for complete search history.

(56) References Cited

U.S. PATENT DOCUMENTS

| 4,652,441 | A |   | 3/1987 | Okada et al. |
|---|---|---|---|---|
| 4,835,139 | A | * | 5/1989 | Tice et al. ................. 514/9.9 |
| 4,849,228 | A | * | 7/1989 | Yamamoto et al. ........... 424/502 |
| 4,938,763 | A |   | 7/1990 | Dunn et al. |
| 5,198,220 | A |   | 3/1993 | Damani |
| 5,702,716 | A | * | 12/1997 | Dunn et al. ................. 424/422 |
| 5,747,637 | A |   | 5/1998 | Shinoda et al. |
| 6,143,314 | A |   | 11/2000 | Chandrashekar et al. |
| 6,238,687 | B1 |   | 5/2001 | Mao et al. |
| 6,413,536 | B1 |   | 7/2002 | Gibson et al. |
| 6,555,645 | B1 |   | 4/2003 | Ikeda et al. |
| 8,470,359 | B2 |   | 6/2013 | Dunn |
| 8,486,455 | B2 |   | 7/2013 | Dunn et al. |
| 8,840,916 | B2 |   | 9/2014 | Dunn et al. |
| 2007/0117959 | A1 |   | 5/2007 | Shastri et al. |
| 2010/0226954 | A1 |   | 9/2010 | Dunn et al. |

FOREIGN PATENT DOCUMENTS

| EP | 0052510 A2 | * | 5/1982 |
|---|---|---|---|
| EP | 0430474 A1 |   | 6/1991 |
| EP | 0539751 A1 |   | 5/1993 |
| JP | 03/271213 A |   | 12/1991 |
| JP | 03/271219 A |   | 12/1991 |
| JP | 05/305135 A |   | 11/1993 |
| JP | 09/511741 A |   | 11/1997 |
| WO | WO 00/40259 | * | 7/2000 |

OTHER PUBLICATIONS

"U.S. Appl. No. 11/469,392, Response filed Sep. 27, 2011 to Non Final Office Action Mailed Jul. 5, 2011", 17 pgs.
"U.S. Appl. No. 11/469,392, Advisory Action mailed Mar. 16, 2011", 3 pgs.
"U.S. Appl. No. 11/469,392, Final Office Action mailed Jul. 5, 2011", 8 pgs.
"U.S. Appl. No. 11/469,392, Final Office Action mailed Dec. 29, 2010", 11 pgs.
"U.S. Appl. No. 11/469,392, Non-Final Office Action mailed Jul. 20, 2010", 9 pgs.
"U.S. Appl. No. 11/469,392, Response filed Feb. 24, 2011 to Final Office Action mailed Dec. 29, 2010", 14 pgs.
"U.S. Appl. No. 11/469,392, Response filed May 31, 2011 to Advisory Action mailed Mar. 16, 2011", 23 pgs.
"U.S. Appl. No. 11/469,392, Response filed Jun. 30, 2010 to Restriction Requirement mailed Jun. 9, 2010", 10 pgs.
"U.S. Appl. No. 11/469,392, Response filed Oct. 7, 2010 to Non Final Office Action mailed Jul. 20, 2010", 14 pgs.
"Appl. No. 11/469,392, Restriction Requirement mailed Jun. 9, 2010", 7 pgs.
"Application Serial No. 2000-577985 Office Action mailed Mar. 16, 2010", (w/ English Translation), 14 pgs.
"Application Serial No. 2000-577985 Response filed Jul. 2, 2010 to Office Action mailed Mar. 16, 2010", (w/ English Translation of Amended Claims), 11 pgs.
"Japanese Application Serial No. 2006-543949, Notice of Allowance mailed Aug. 5, 2010", 3 pgs.

(Continued)

*Primary Examiner* — Michael G Hartley
*Assistant Examiner* — Robert Cabral
(74) *Attorney, Agent, or Firm* — Schwegman Lundberg & Woessner, P.A.

(57) ABSTRACT

The present invention is directed to a flowable composition that is suitable for use as a controlled release implant. The flowable composition includes a biodegradable thermoplastic polyester that is at least substantially insoluble in aqueous medium or body fluid. The flowable composition also includes a biocompatible polar aprotic solvent. The biocompatible polar aprotic solvent is miscible to dispersible in aqueous medium or body fluid. The flowable composition also includes leuprolide acetate.

3 Claims, 5 Drawing Sheets

(56) References Cited

OTHER PUBLICATIONS

*In: Goodman & Gilman's The Pharmacological Basis of Therapeutics*, Tenth Edition. McGraw-Hill, (2001), 3-5, 24-25, 31-34.
"Additional experimental data", (submitted Nov. 19, 2014), 6 pgs.
"U.S. Appl. No. 13/900,338, Notice of Allowance mailed May 21, 2014", 5 pgs.
"U.S. Appl. No. 13/900,338, Response filed Apr. 15, 2014 to Final Office Action mailed Apr. 11, 2014", 3 pgs.
"U.S. Appl. No. 14/463,353, Preliminary Amendment filed Aug. 20, 2014", 6 pgs.
"Lupron Depot(r)", *Physicians' Desk Reference®, 53rd Edition*, published by Medical Economics Company, Inc., Montvale, NJ, (1999), 3139-3150.
"Lupron®, TAP Pharmaceuticals, Inc.", *Physicians' Desk Reference®, 54th Edition*, published by Medical Economics Company, Inc., Montvale, NJ, (2000), 3 pgs.
Astaneh, Reyhaneh, et al., "Formulation of an Injectable Implant for Peptide Delivery and Mechanistic Study of the Effect of Polymer Molecular Weight on its Release Behavior", *DARU*, 14(2), (2006), 65-70.
Heller, J., "Controlled release of biologically active compounds from bioerodible polymers", *Biomaterials*, 1(1), (Jan. 1980), 51-57.
Jalil, R., et al., "Biodegradable poly(lactic acid) and poly(lactide-co-glycolide) microcapsules: problems associated with preparative techniques and release properties", *J. Microencapsulation*, 7(3), (1990), 297-325.
Sharifi, R., et al., "Clinical study of leuprolide depot formulation in the treatment of advanced prostate cancer. The Leuprolide Study Group", *The Journal of Urology*, 143(1), (Jan. 1990). 68-71.
Tice, T. R., et al., "Biodegradable controlled-release parental systems", *Pharmaceutical Technology*, 8(11), (Nov. 1984), 26-35.
Wise, Donald L., et al., "Chapter 12—Lactic/Glycolic Acid Polymers", *In: Drug Carriers in Biology and Medicine*, Gregoriadis, G., Editor, Academic Press, Inc. New York, NY, (1979), 237-270.
"U.S. Appl. No. 11/469,392, Notice of Allowance mailed Feb. 27, 2013", 9 pgs.
"U.S. Appl. No. 12/784,304, Notice of Allowance mailed May 28, 2013", 9 pgs.
"U.S. Appl. No. 13/900,338, Non Final Office Action mailed Sep. 23, 2013", 7 pgs.
"U.S. Appl. No. 13/900,338, Preliminary Amendment filed Aug. 22, 2013", 7 pgs.
"U.S. Appl. No. 09/181,355, Advisory Action mailed Mar. 16, 2000", 3 pgs.
"U.S. Appl. No. 09/181,355, Final Office Action mailed Nov. 23, 1999", 10 pgs.
"U.S. Appl. No. 09/181,355, Notice of Allowance mailed May 31, 2000", 7 pgs.
"U.S. Appl. No. 09/181,355, Response filed Feb. 23, 2000 to Final Office Action mailed Nov. 23, 1999", 7 pgs.
"U.S. Appl. No. 09/181,355, Response filed Apr. 20, 2000 to Advisory Action mailed Mar. 16, 2000", 6 pgs.
"U.S. Appl. No. 09/643,289, Advisory Action mailed Jul. 30, 2002", 2 pgs.
"U.S. Appl. No. 09/643,289, Final Office Action mailed Mar. 20, 2002", 8 pgs.
"U.S. Appl. No. 09/643,289, Non Final Office Action mailed May 25, 2001", 8 pgs.
"U.S. Appl. No. 09/643,289, Non Final Office Action mailed Nov. 13, 2002", 5 pgs.
"U.S. Appl. No. 09/643,289, Notice of Allowance mailed May 6, 2003", 6 pgs.
"U.S. Appl. No. 09/643,289, PTO Response to 312 Amendment mailed Aug. 6, 2003", 2 pgs.
"U.S. Appl. No. 09/643,289, Response filed Feb. 26, 2003 to Non Final Office Action mailed Nov. 13, 2002", 15 pgs.
"U.S. Appl. No. 09/643,289, Response filed Jun. 20, 2002 to Final Office Action mailed Mar. 20, 2002", 20 pgs.
"U.S. Appl. No. 09/643,289, Response filed Nov. 20, 2001 to Non Final Office Action mailed May 5, 2001", 23 pgs.
"U.S. Appl. No. 09/666,174, Final Office Action mailed Aug. 10, 2001", 10 pgs.
"U.S. Appl. No. 09/666,174, Non Final Office Action mailed Mar. 19, 2001", 9 pgs.
"U.S. Appl. No. 09/666,174, Response filed Jun. 19, 2001 to Non Final Office Action mailed Mar. 19, 2001", 9 pgs.
"U.S. Appl. No. 09/711,758, 312 Amendment filed Mar. 4, 2003", 2 pgs.
"U.S. Appl. No. 09/711,758, Final Office Action mailed Feb. 4, 2002", 10 pgs.
"U.S. Appl. No. 09/711,758, Non Final Office Action mailed Jun. 17, 2002", 8 pgs.
"U.S. Appl. No. 09/711,758, Non Final Office Action mailed Jul. 2, 2001", 10 pgs.
"U.S. Appl. No. 09/711,758, Notice of Allowance mailed Jan. 8, 2003", 6 pgs.
"U.S. Appl. No. 09/711,758, PTO Resonse to 312 Amendment mailed Apr. 13, 2003", 2 pgs.
"U.S. Appl. No. 09/711,758, Response filed May 6, 2002 to Final Office Action mailed Feb. 4, 2002", 17 pgs.
"U.S. Appl. No. 09/711,758, Response filed Oct. 14, 2002 to Non Final Office Action mailed Jun. 17, 2002", 13 pgs.
"U.S. Appl. No. 09/711,758, Response filed Nov. 2, 2001 to Non Final Office Action mailed Jul. 2, 2001", 105 pgs.
"U.S. Appl. No. 10/373,400, Non Final Office Action mailed Oct. 28, 2003", 8 pgs.
"U.S. Appl. No. 10/373,400, Notice of Allowance mailed Mar. 18, 2004", 5 pgs.
"U.S. Appl. No. 10/373,400, Preliminary Amendment filed Apr. 3, 2003", 2 pgs.
"U.S. Appl. No. 10/373,400, Response filed Feb. 20, 2004 to Non Final Office Action mailed Oct. 28, 2003", 17 pgs.
"U.S. Appl. No. 10/872,671, Non Final Office Action mailed May 4, 2006", 10 pgs.
"U.S. Appl. No. 10/872,671, Response filed Oct. 4, 2006 to Non Final Office Action mailed May 4, 2006", 10 pgs.
"U.S. Appl. No. 11/469,392 , Response filed Jan. 13, 2012 to Final Office Action mailed Dec. 21, 2011", 12 pgs.
"U.S. Appl. No. 11/469,392, Advisory Action mailed Feb. 8, 2012", 3 pgs.
"U.S. Appl. No. 11/469,392, Final Office Action mailed Dec. 21, 2011", 8 pgs.
"U.S. Appl. No. 11/469,392, Preliminary Amendment mailed Mar. 1, 2012", 12 pgs.
"U.S. Appl. No. 11/643,505, Preliminary Amendment filled Dec. 21, 2006", 5 pgs.
"U.S. Appl. No. 12/784,304, Non Final Office Action mailed Mar. 6, 2012", 5 pgs.

* cited by examiner

POLYMERIC DELIVERY FORMULATIONS OF LEUPROLIDE WITH IMPROVED EFFICACY

CROSS-REFERENCE TO RELATED APPLICATIONS

This application is a continuation of U.S. patent application Ser. No. 11/643,505, filed Dec. 21, 2006, which is a continuation of U.S. patent application Ser. No. 10/872,671, filed Jun. 21, 2004, which is a continuation of U.S. patent application Ser. No.10/373,400, filed Feb. 24, 2003which is a continuation of U.S. application Ser. No. 09/711,758, filed Nov. 13, 2000and issued as U.S. Pat. No. 6,565,874, which is a continuation-in-part of U.S. patent application Ser. No. 09/666,174, filed on Sep. 21, 2000 and a continuation-in-part of U.S. patent application Ser. No. 09/643,289, filed Aug. 22, 2000 and issued as U.S. Pat. No. 6,630,155, which in turn is a continuation application of U.S. patent application Ser. No. 09/181,355, filed Oct. 28, 1998 and issued as U.S. Pat. No. 6,143,314, which are incorporated herein by reference.

BACKGROUND OF THE INVENTION

Leuprolide acetate is an LHRH agonist analog that is useful in the palliative treatment of hormonal related prostate cancer, mammary cancer, endometriosis, and precocious puberty. With continued use, leuprolide acetate causes pituitary desnsitizing and down-regulation to affect the pituitary-gonodal axis, leading to suppressed circulating levels of luteinizing and sex hormones. In patients with advanced prostate cancer, achieving circulating testosterone levels of less than or equal to 0.5 ng/ml (chemical castration level) is a desired pharmacological indicator of therapeutic action.

Originally, leuprolide acetate was launched in the United States as a daily subcutaneous (s.c.) injection of the analog solution. The inconvenience of chronic repetitive injections was later eliminated by the development of a one month sustained release depot product based on poly(DL-lactide-co-glycolide) microspheres (Lupron® Depot). Currently, one, three, and four month formulations are widely available as intramuscular (i.m.) injections of microspheres.

Although the current Lupron® Depot microspheres appear to be effective, the microsphere products are difficult to manufacture, and they all require a deep intramuscular (i.m.) injection using large volumes of fluid to ensure that all of the microspheres are properly administered to the patient. These injections are often painful and lead to tissue damage.

Biodegradable polymers other than Lupron® Depot have been employed in many medical applications, including drug delivery devices. The drug is generally incorporated into the polymeric composition and formed into the desired shape outside the body. This solid implant is then typically inserted into the body of a human, animal, bird, and the like through an incision. Alternatively, small discrete particles composed of these polymers can be injected into the body by a syringe. Preferably, however, certain of these polymers can be injected via syringe as a liquid polymeric composition.

Liquid polymeric compositions useful for biodegradable controlled release drug delivery systems are described, e.g., in U.S. Pat. Nos. 4,938,763; 5,702,716; 5,744,153; 5,990,194; and 5,324,519. These compositions are administered to the body in a liquid state or, alternatively, as a solution, typically via syringe. Once in the body, the composition coagulates into a solid. One type of polymeric composition includes a nonreactive thermoplastic polymer or copolymer dissolved in a body fluid-dispersible solvent. This polymeric solution is placed into the body where the polymer congeals or precipitatively solidifies upon the dissipation or diffusion of the solvent into the surrounding body tissues. It is expected that these compositions would be as effective as Lupron® Depot, since leuprolide of these compositions is the same as are in the Lupron® Depot and the polymers are similar.

Surprisingly, however, it has been discovered that the liquid polymeric compositions according to the present invention are more effective in delivering leuprolide acetate than Lupron® Depot. Specifically, the testosterone levels obtained with the liquid polymeric compositions of the present invention containing the leuprolide acetate are lower at extended times in dogs compared to Lupron® Depot, and also at the six month point in humans, compared to the value reported in the literature for Lupron® Depot (Sharifi, R., *J. Urology*, Vol. 143, Jan., 68 (1990)).

SUMMARY OF THE INVENTION

The present invention provides a flowable composition that is suitable for use as a controlled release implant of leuprolide acetate. The flowable composition includes a biodegradable thermoplastic polyester that is at least substantially insoluble in an aqueous medium or body fluid. The flowable composition also includes a biocompatible polar aprotic solvent. The biocompatible polar aprotic solvent can be an amide, an ester, a carbonate, a ketone, an ether, or a sulfonyl. The biocompatible polar aprotic solvent is miscible to dispersible in aqueous medium or body fluid. The flowable composition also includes leuprolide acetate. The leuprolide acetate is preferably present in about 2 wt. % to about 4 wt. % of the composition or in about 4 wt. % to about 8 wt. % of the composition. Preferably, the flowable composition is formulated as an injectable subcutaneous delivery system. The injectable composition preferably has a volume of about 0.20 mL to about 0.40 mL or about 0.30 mL to about 0.50 mL. The injectable composition is preferably formulated for administration about once per month, about once per three months, or about once per four months to about once per six months. Preferably, the flowable composition is a liquid or a gel composition, suitable for injection into a patient.

Preferably, the biodegradable thermoplastic polyester is a polylactide, a polyglycolide, a polycaprolactone, a copolymer thereof, a terpolymer thereof, or any combination thereof. More preferably, the biodegradable thermoplastic polyester is a polylactide, a polyglycolide, a copolymer thereof, a terpolymer thereof, or a combination thereof. More preferably, the suitable biodegradable thermoplastic polyester is 50/50 poly (DL-lactide-co-glycolide) having a carboxy terminal group or is 75/25 poly (DL-lactide-co-glycolide) with a carboxy terminal group that is protected. The suitable biodegradable thermoplastic polyester can be present in any suitable amount, provided the biodegradable thermoplastic polyester is at least substantially insoluble in aqueous medium or body fluid. The suitable biodegradable thermoplastic polyester is preferably present in about 30 wt % to about 40 wt. % of the flowable composition or is present in about 40 wt. % to about 50 wt. % of the flowable composition. Preferably, the biodegradable thermoplastic polyester has an average molecular weight of about 23,000 to about 45,000 or about 15,000 to about 24,000.

Preferably, the biocompatible polar aprotic solvent is N-methyl-2-pyrrolidone, 2-pyrrolidone, N, N-dimethylformamide, dimethyl sulfoxide, propylene carbonate, caprolactam, triacetin, or any combination thereof. More preferably, the biocompatible polar aprotic solvent is N-methyl-2-pyrrolidone. Preferably, the polar aprotic solvent is present in about 60 wt. % to about 70 wt. % of the composition or is present in about 45 wt. % to about 55 wt. % of the composition.

The present invention also provides for a method for forming a flowable composition. The flowable composition is useful as a controlled release implant. The method includes mixing, in any order, a biodegradable thermoplastic polyester, a biocompatible polar aprotic solvent, and leuprolide acetate. These ingredients, their properties, and preferred amounts are as disclosed above. The mixing is performed for a sufficient period of time effective to form the flowable composition for use as a controlled release implant. Preferably, the biocompatible thermoplastic polyester and the biocompatible polar aprotic solvent are mixed together to form a mixture and the mixture is then combined with the leuprolide acetate to form the flowable composition.

The present invention also provides for a biodegradable implant formed in situ, in a patient. The biodegradable implant product is prepared by the process of injecting a flowable composition within the body of the patient and allowing the biocompatible polar aprotic solvent to dissipate to produce a solid biodegradable implant. These ingredients, their properties, and preferred amounts are as disclosed above. Preferably, the patient is a human. The solid implant preferably releases the effective amount of leuprolide as the solid implant biodegrades in the patient.

The present invention also provides for a method of forming a biodegradable implant in situ, in a living patient. The method includes injecting the flowable composition of the present invention within the body of a patient and allowing the biocompatible polar aprotic solvent to dissipate to produce a solid biodegradable implant. The flowable composition includes an effective amount of a biodegradable thermoplastic polyester, an effective amount of a biocompatible polar aprotic solvent, and an effective amount of leuprolide acetate. These ingredients, their properties, and preferred amounts are as disclosed above. Preferably, the solid biodegradable implant releases the effective amount of leuprolide acetate by diffusion, erosion, or a combination of diffusion and erosion as the solid implant biodegrades in the patient.

The present invention also provides a method of treating or preventing cancer in a patient. The method includes administering to the patient in need of such treatment or prevention an effective amount of a flowable composition of the present invention. Specifically, the cancer can be prostate cancer. In addition, the patient can be a human.

The present invention also provides a method of reducing LH levels in a patient. The method includes administering to the patient in need of such LH reduction an effective amount of a flowable composition of the present invention. Specifically, the reduction of LH levels can be useful to treat endometriosis. In addition, the patient can be a human.

The present invention also provides a kit. The kit includes a first container and a second container. The first container includes a composition that includes the biodegradable thermoplastic polyester and the biocompatible polar aprotic solvent. The second container includes leuprolide acetate. These ingredients, their properties, and preferred amounts are as disclosed above. Preferably, the first container is a syringe and the second container is a syringe. In addition, the leuprolide acetate is preferably lyophilized. The kit can preferably include instructions. Preferably, the first container can be connected to the second container. More preferably, the first container and the second container are each configured to be directly connected to each other.

The present invention also provides a solid implant. The solid implant includes a biocompatible thermoplastic polyester and leuprolide acetate. The biocompatible thermoplastic polyester is at least substantially insoluble in aqueous medium or body fluid. The solid implant has a solid or gelatinous microporous matrix, wherein the matrix is a core surrounded by a skin. The solid implant can further include a biocompatible organic solvent. The biocompatible organic solvent is preferably miscible to dispersible in aqueous or body fluid. In addition, the biocompatible organic solvent preferably dissolves the thermoplastic polyester. The amount of biocompatible organic solvent, if present, is preferably minor, such as from 0 wt. % to about 20 wt. % of the composition. In addition, the amount of biocompatible organic solvent preferably decreases over time. The core preferably contains pores of diameters from about 1 to about 1000 microns. The skin preferably contains pores of smaller diameters than those of the core pores. In addition, the skin pores are preferably of a size such that the skin is functionally non-porous in comparison with the core.

DETAILED DESCRIPTION OF THE INVENTION

Figure 1:
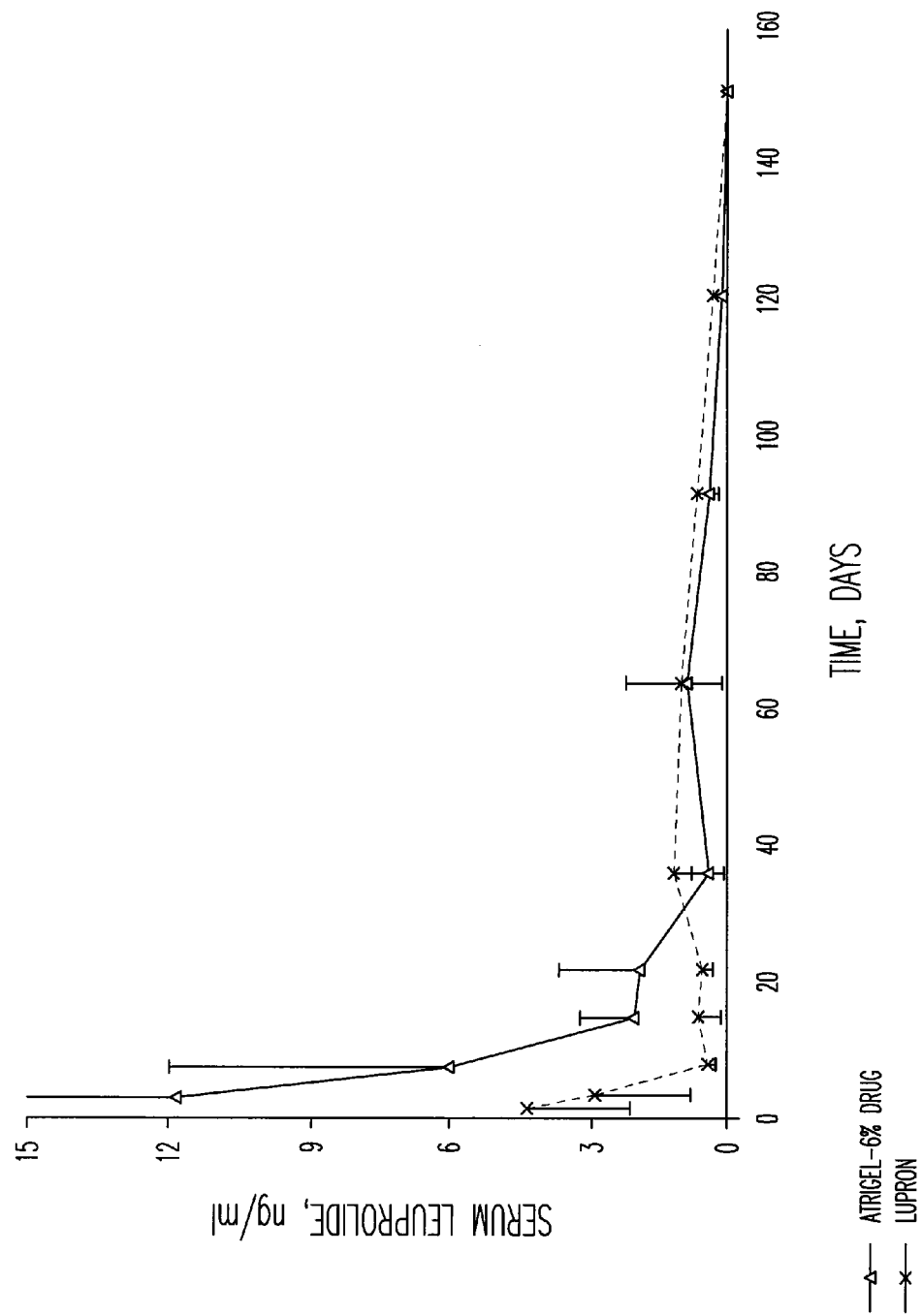
FIG. 1 illustrates serum leuprolide levels in dogs after administering ATRIGEL®-6% w/w drug and Lupron® formulations.
Figure 2:
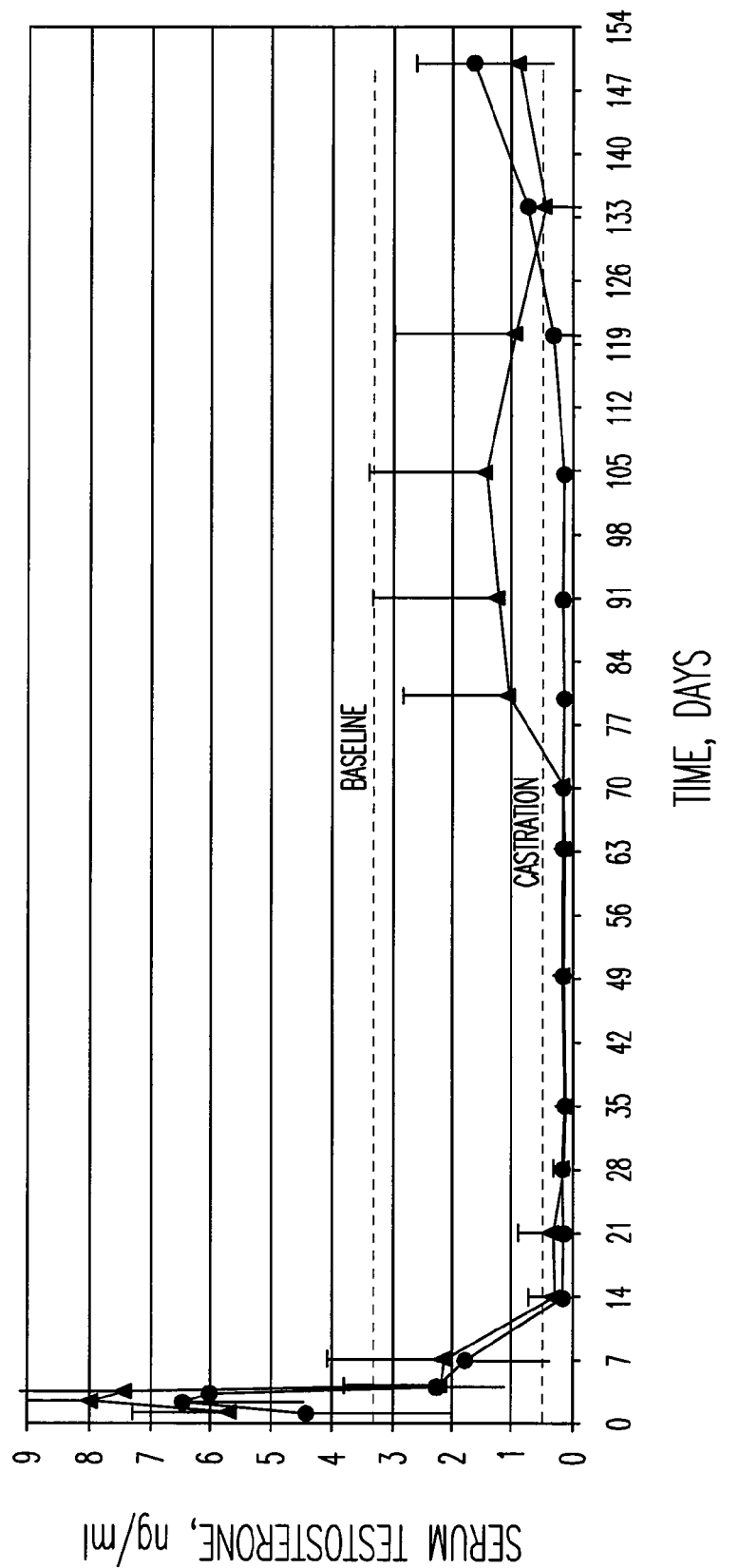
FIG. 2 illustrates testosterone suppression in dogs with ATRIGEL® and Lupron® 90 day formulations.

Specific and preferred biodegradable thermoplastic polyesters and polar aprotic solvents; ranges of thermoplastic polyesters, polar aprotic solvents, leuprolide acetate, and flowable compositions; molecular weights of the thermoplastic polyester; and ranges of the solid implant described herein below are for illustration only; they do not exclude other biodegradable thermoplastic polyesters and polar aprotic solvents; ranges of thermoplastic polyesters, polar aprotic solvents, leuprolide acetate, and flowable compositions; molecular weights of the thermoplastic polyester; and ranges of the solid implant.

The present invention provides a flowable composition suitable for use as a controlled release implant, a method for forming the flowable composition, a method for using the flowable composition, the biodegradable implant that is formed in situ from the flowable composition, a method of forming the biodegradable implant in situ, a method for using the biodegradable implant that is formed in situ, a kit that includes the flowable composition, and the solid implant. The flowable composition may be used to provide a biodegradable or bioerodible microporous in situ formed implant in animals. The flowable composition is composed of a biodegradable thermoplastic polymer or copolymer in combination with a suitable polar aprotic solvent. The biodegradable thermoplastic polyesters or copolymers are substantially insoluble in water and body fluid, biocompatible, and biodegradable and/or bioerodible within the body of an animal. The flowable composition is administered as a liquid or gel to tissue wherein the implant is formed in situ. The composition is biocompatible and the polymer matrix does not cause substantial tissue irritation or necrosis at the implant site. The implant can be used to deliver leuprolide acetate.

Preferably, the flowable composition can be a liquid or a gel, suitable for injection in a patient (e.g., human). As used herein, "flowable" refers to the ability of the composition to be injected through a medium (e.g., syringe) into the body of a patient. For example, the composition can be injected, with the use of a syringe, beneath the skin of a patient. The ability of the composition to be injected into a patient will typically depend upon the viscosity of the composition. The composition will therefore have a suitable viscosity, such that the composition can be forced through the medium (e.g., syringe) into the body of a patient. As used herein, a "liquid" is a substance that undergoes continuous deformation under a shearing stress. *Concise Chemical and Technical Dictionary*, 4th Enlarged Ed., Chemical Publishing Co., Inc., p. 707, NY, N.Y. (1986). As used herein, a "gel" is a substance having a gelatinous, jelly-like, or colloidal properties. *Concise Chemical and Technical Dictionary*, 4th Enlarged Ed., Chemical Publishing Co., Inc., p. 567, NY, N.Y. (1986).

Biodegradable Thermoplastic Polyester

A thermoplastic composition is provided in which a solid, biodegradable polyester and leuprolide acetate are dissolved in a biocompatible polar aprotic solvent to form a flowable composition, which can then be administered via a syringe and needle. Any suitable biodegradable thermoplastic polyester can be employed, provided the biodegradable thermoplastic polyester is at least substantially insoluble in aqueous medium or body fluid. Suitable biodegradable thermoplastic polyesters are disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The type, molecular weight, and amount of biodegradable thermoplastic polyester present in the composition will typically depend upon the desired properties of the controlled release implant. For example, the type, molecular weight, and amount of biodegradable thermoplastic polyester can influence the length of time in which the leuprolide acetate is released from the controlled release implant. Specifically, in one embodiment of the present invention, the composition can be used to formulate a one month delivery system of leuprolide acetate. In such an embodiment, the biodegradable thermoplastic polyester can preferably be 50/50 poly (DL-lactide-co-glycolide) having a carboxy terminal group; can be present in about 30 wt. % to about 40 wt. % of the composition; and can have an average molecular weight of about 23,000 to about 45,000. Alternatively, in another embodiment of the present invention, the composition can be used to formulate a three month delivery system of leuprolide acetate. In such an embodiment, the biodegradable thermoplastic polyester can preferably be 75/25 poly (DL-lactide-co-glycolide) without a carboxy terminal group; can be present in about 40 wt. % to about 50 wt. % of the composition; and can have an average molecular weight of about 15,000 to about 24,000.

The terminal groups of the poly(DL-lactide-co-glycolide) can either be hydroxyl, carboxyl, or ester depending upon the method of polymerization. Polycondensation of lactic or glycolic acid will provide a polymer with terminal hydroxyl and carboxyl groups. Ring-opening polymerization of the cyclic lactide or glycolide monomers with water, lactic acid, or glycolic acid will provide polymers with the same terminal groups. However, ring-opening of the cyclic monomers with a monofunctional alcohol such as methanol, ethanol, or 1-dodecanol will provide a polymer with one hydroxyl group and one ester terminal groups. Ring-opening polymerization of the cyclic monomers with a diol such as 1,6-hexanediol or polyethylene glycol will provide a polymer with only hydroxyl terminal groups.

Thermoplastic Polyester Molecular Weight

The molecular weight of the polymer used in the present invention can affect the rate of leuprolide acetate release as long as the flowable composition has been used as an intermediate. Under these conditions, as the molecular weight of the polymer increases, the rate of leuprolide acetate release from the system decreases. This phenomenon can be advantageously used in the formulation of systems for the controlled release of leuprolide acetate. For relatively quick release of leuprolide acetate, low molecular weight polymers can be chosen to provide the desired release rate. For release of a leuprolide acetate over a relatively long period of time, a higher polymer molecular weight can be chosen. Accordingly, a polymer system can be produced with an optimum polymer molecular weight range for the release of leuprolide acetate over a selected length of time.

The molecular weight of a polymer can be varied by any of a variety of methods. The choice of method is typically determined by the type of polymer composition. For example, if a thermoplastic polyester is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

Polar Aprotic Solvent

Any suitable polar aprotic solvent can be employed, provided the suitable polar aprotic solvent is miscible to dispersible in aqueous medium or body fluid. Suitable polar aprotic solvents are disclosed, e.g., in *Aldrich Handbook of Fine Chemicals and Laboratory Equipment*, Milwaukee, Wis. (2000); U.S. Pat. Nos. 5,324,519; 4,938,763; 5,702,716; 5,744,153; and 5,990,194. The suitable polar aprotic solvent should be able to diffuse into body fluid so that the flowable composition coagulates or solidifies. It is also preferred that the polar aprotic solvent for the biodegradable polymer be non-toxic and otherwise biocompatible. The polar aprotic solvent is preferably biocompatible. Examples of suitable polar aprotic solvents include polar aprotic solvents having an amide group, an ester group, a carbonate group, a ketone, an ether, a sulfonyl group, or a combination thereof. Preferably, the polar aprotic solvent can be N-methyl-2-pyrrolidone, 2-pyrrolidone, N,N-dimethylformamide, dimethyl sulfoxide, propylene carbonate, caprolactam, triacetin, or any combination thereof. More preferably, the polar aprotic solvent can be N-methyl-2-pyrrolidone.

The polar aprotic solvent can be present in any suitable amount, provided the polar aprotic solvent is miscible to dispersible in aqueous medium or body fluid. The type and amount of biocompatible polar aprotic solvent present in the composition will typically depend upon the desired properties of the controlled release implant. For example, the type and amount of biocompatible polar aprotic solvent can influence the length of time in which the leuprolide acetate is released from the controlled release implant. Specifically, in one embodiment of the present invention, the composition can be used to formulate a one month delivery system of leuprolide acetate. In such an embodiment, the biocompatible polar aprotic solvent can preferably be N-methyl-2-pyrrolidone and can preferably present in about 60 wt. % to about 70 wt. % of the composition. Alternatively, in another embodiment of the present invention, the composition can be used to formulate a three month delivery system of leuprolide acetate. In such an embodiment, the biocompatible polar aprotic solvent can preferably be N-methyl-2-pyrrolidone and can preferably present in about 50 wt. % to about 60 wt. % of the composition.

The solubility of the biodegradable thermoplastic polyesters in the various polar aprotic solvents will differ depending upon their crystallinity, their hydrophilicity, hydrogen-bonding, and molecular weight. Thus, not all of the biodegradable thermoplastic polyesters will be soluble in the same polar aprotic solvent, but each biodegradable thermoplastic polymer or copolymer should have its appropriate polar aprotic solvent. Lower molecular-weight polymers will normally dissolve more readily in the solvents than high-molecular-weight polymers. As a result, the concentration of a polymer dissolved in the various solvent will differ depending upon type of polymer and its molecular weight. Conversely, the higher molecular-weight polymers will normally tend to coagulate or solidify faster than the very low-molecular-weight polymers. Moreover the higher molecular-weight polymers will tend to give higher solution viscosities than the low-molecular-weight materials.

For example, low-molecular-weight polylactic acid formed by the condensation of lactic acid will dissolve in N-methyl-2-pyrrolidone(NMP) to give a 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in NMP at only 50% by weight. The higher molecular-weight polymer solution coagulates immediately when placed into water. The low-molecular-weight polymer solution, although more concentrated, tends to coagulate very slowly when placed into water.

It has also been found that solutions containing very high concentrations of high-molecular-weight polymers sometimes coagulate or solidify slower than more dilute solutions. It is suspected that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

The leuprolide acetate is preferably lyophilized prior to use. Typically, the leuprolide acetate can be dissolved in an aqueous solution, sterile filtered, and lyophilized in a syringe. The polymer/solvent solution can be filled into another syringe. The two syringes can then be coupled together and the contents can be drawn back and forth between the two syringes until the polymer/solvent solution and the leuprolide acetate are effectively mixed together, forming a flowable composition. The flowable composition can be drawn into one syringe. The two syringes can then be disconnected. A needle can be inserted onto the syringe containing the flowable composition. The flowable composition can then be injected through the needle into the body. The flowable composition can be formulated and administered to a patient as described in, e.g., U.S. Pat. Nos. 5,324,519; 4,938,763; 5,702,716; 5,744,153; and 5,990,194; or as described herein. Once in place, the solvent dissipates, the remaining polymer solidifies, and a solid structure is formed. The solvent will dissipate and the polymer will solidify and entrap or encase the leuprolide acetate within the solid matrix.

The release of leuprolide acetate from these solid implants will follow the same general rules for release of a drug from a monolithic polymeric device. The release of leuprolide acetate can be affected by the size and shape of the implant, the loading of leuprolide acetate within the implant, the permeability factors involving the leuprolide acetate and the particular polymer, and the degradation of the polymer. Depending upon the amount of leuprolide acetate selected for delivery, the above parameters can be adjusted by one skilled in the art of drug delivery to give the desired rate and duration of release.

The amount of leuprolide acetate incorporated into the flowable, in-situ, solid forming implant depends upon the desired release profile, the concentration of leuprolide acetate required for a biological effect, and the length of time that the leuprolide acetate has to be released for treatment. There is no critical upper limit on the amount of leuprolide acetate incorporated into the polymer solution except for that of an acceptable solution or dispersion viscosity for injection through a syringe needle. The lower limit of leuprolide acetate incorporated into the delivery system is dependent simply upon the activity of the leuprolide acetate and the length of time needed for treatment. Specifically, in one embodiment of the present invention, the composition can be used to formulate a one month delivery system of leuprolide acetate. In such an embodiment, the leuprolide acetate can preferably be present in about 2 wt. % to about 4 wt. % of the composition. Alternatively, in another embodiment of the present invention, the composition can be used to formulate a three month delivery system of leuprolide acetate. In such an embodiment, the leuprolide acetate can preferably be present in about 4 wt. % to about 8 wt. % of the composition. The solid implant formed from the flowable system will release the leuprolide acetate contained within its matrix at a controlled rate until the leuprolide acetate is effectively depleted.

Dosages

The amount of flowable composition administered will typically depend upon the desired properties of the controlled release implant. For example, the amount of flowable composition can influence the length of time in which the leuprolide acetate is released from the controlled release implant. Specifically, in one embodiment of the present invention, the composition can be used to formulate a one month delivery system of leuprolide acetate. In such an embodiment, about 0.20 mL to about 0.40 mL of the flowable composition can be administered. Alternatively, in another embodiment of the present invention, the composition can be used to formulate a three month delivery system of leuprolide acetate. In such an embodiment, about 0.30 mL to about 0.50 mL of the flowable composition can be administered.

Surprisingly, it has been discovered that the liquid polymeric compositions according to the present invention are more effective in delivering leuprolide acetate than Lupron® Depot. Specifically, as shown in the Examples below, the testosterone levels obtained with the liquid polymeric compositions of the present invention containing the leuprolide acetate are lower at extended times in dogs compared to Lupron® Depot, and also at the six month point in humans, compared to the value reported in the literature for Lupron® Depot (Sharifi, R., *J. Urology*, Vol. 143, Jan., 68 (1990)).

All publications, patents, and patent documents are incorporated by reference herein, as though individually incorporated by reference. The invention will now be illustrated with the following non-limiting examples.

EXAMPLES

Example 1

Poly(DL-lactide-co-glycolide) having a 50/50 ratio of lactide to glycolide and a terminal carboxyl group (RG 504H from Boehringer Ingelheim) was dissolved in N-methyl-2-pyrrolidone (NMP) to give a 34% by weight polymer solution. This ATRIGEL® polymer solution was filled into 1.25 cc polypropylene syringes with a female luer lock fitting at a volume of 330 CL and terminally sterilized by exposure to gamma irradiation at 20 kilograys. The molecular weight of the polymer after gamma irradiation was 32,000 daltons. Leuprolide acetate was dissolved in water, sterile filtered through a 0.2 cm filter, and filled into a 1.00 cc polypropylene syringe with a male luer-lock fitting. The aqueous solution was frozen and the water removed under vacuum to give a 10.2 mg lyophilized cake of the peptide. The two syringes were coupled just prior to use and the contents mixed back and forth between the two syringes for 30 cycles. The formulation was drawn back into the syringe with the male coupling, the two syringes separated, and a one-half inch 20 gauge needle was attached. The contents of the syringe were then injected subcutaneously into 7 male beagle dogs to give a total of 250 mg of polymer formulation containing 7.5 mg of leuprolide acetate. Lupron® Depot microspheres with 7.5 mg of leuprolide acetate were injected intramuscularly into a second set of 7 beagle dogs. Serum samples were collected from all of the dogs at baseline and days 1, 3, 7, 14, 21, 28, 35, 42, 49, 55, 63, 77, and 91.

The serum samples were analyzed for testosterone using an RIA method. The results given in Table 1 show that both products are effective in lowering the testosterone concentrations below the human castrate level of 0.5 ng/mL after about 14 days, and maintaining this effect out to day 42. Overall, it appeared that the testosterone levels obtained with the Lupron® Depot were slightly lower than those observed with the ATRIGEL® polymer system.

TABLE 1

Serum Testosterone Data in Dogs

| Time, Days | Testosterone Levels, ng/mL | |
|---|---|---|
| | ATRIGEL ® | Lupron ® |
| 1 | 2.23 | 3.52 |
| 3 | 5.50 | 4.85 |
| 7 | 0.47 | 1.05 |
| 14 | 0.60 | 0.39 |
| 21 | 0.36 | 0.07 |
| 28 | 0.24 | 0.08 |
| 35 | 0.15 | 0.07 |
| 42 | 0.51 | 0.31 |
| 49 | 2.09 | 0.30 |
| 55 | 2.85 | 1.08 |
| 63 | 4.95 | 0.77 |
| 77 | 4.82 | 1.22 |
| 91 | 2.23 | 2.84 |

Example 2

The same polymer solution as described in Example 1 was sterile filtered through a 0.2 cm filter to give a polymer formulation with a molecular weight of 48,000 daltons. The sterile polymer solution was then filled aseptically into the female polypropylene syringes. Also, the same bulk polymer solution before sterile filtration was divided into four different samples, filled into polypropylene syringes and exposed to gamma irradiation at four irradiation levels to degrade the polymer to different molecular weights. The polymer after irradiation at the different dosage levels had molecular weights of 33,500, 26,500, 23,000, and 20,000 daltons. All five formulations were combined with leuprolide acetate as described above and injected subcutaneously into male beagle dogs. Determination of serum testosterone over a 45-day period showed that all of the formulations were effective in reducing the testosterone concentrations below castrate levels except for the formulation with the lowest molecular weight of 20,000 daltons. Thus, the ATRIGEL® polymer formulation containing leuprolide acetate is effective in reducing testosterone for 1 month over a wide range of polymer molecular weights ranging from 23,000 to 45,000 daltons.

Example 3

The polymer formulation described in Example 1 after gamma irradiation at 20 kilograys was combined with leuprolide acetate and injected subcutaneously into 8 male beagle dogs. Lupron® Depot containing 7.5 mg of leuprolide acetate was injected intramuscularly into 8 male beagle dogs. Samples of serum were collected at baseline and days 1, 2, 3, 7, 14, 22, 28, 30, 32, 34, and 36. The serum samples were analyzed for serum testosterone and serum leuprolide by RIA. The values for the serum testosterone concentrations given in Table 2 show that both products were effective in dogs in reducing the testosterone to below human castrate levels with the Lupron® Depot product appearing to be slightly more effective at the later time points. It was thought that the reason for this difference was the higher serum leuprolide levels for the Lupron® Depot product at the intermediate time points as shown in Table 3. Based upon this data, it was anticipated that the ATRIGEL® product with leuprolide would be effective, but perhaps not as efficacious as the Lupron® Depot product.

TABLE 2

Serum Testosterone Data in Dogs

| Time, Days | Testosterone Levels, ng/mL | |
|---|---|---|
| | ATRIGEL ® | Lupron ® |
| 1 | 4.56 | 5.09 |
| 2 | 5.81 | 6.19 |
| 3 | 6.69 | 4.99 |
| 7 | 0.55 | 1.90 |
| 14 | 0.66 | 0.24 |
| 22 | 0.96 | 0.15 |
| 28 | 0.49 | 0.11 |
| 30 | 1.01 | 0.17 |
| 32 | 0.90 | 0.25 |
| 34 | 1.53 | 0.35 |
| 36 | 0.98 | 0.27 |

TABLE 3

Serum Leuprolide Data in Dogs

| Time, Days | Serum Leuprolide Levels, ng/mL | |
|---|---|---|
| | ATRIGEL ® | Lupron ® |
| 1 | 3.98 | 1.94 |
| 2 | 2.34 | 1.41 |
| 3 | 0.81 | 0.93 |

TABLE 3-continued

Serum Leuprolide Data in Dogs

| | Serum Leuprolide Levels, ng/mL | |
|---|---|---|
| Time, Days | ATRIGEL ® | Lupron ® |
| 7 | 1.01 | 1.55 |
| 14 | 0.29 | 1.99 |
| 22 | 0.58 | 2.11 |
| 28 | 0.47 | 0.70 |
| 30 | 0.68 | 0.49 |
| 32 | 0.51 | 0.31 |
| 34 | 0.41 | 0.53 |
| 36 | 0.25 | 0.18 |

Example 4

The polymer formulation described in Example 1 was prepared under GMP conditions, loaded into syringes, and irradiated at 20 kilograys. The sterile polymer solution was then combined with leuprolide acetate which had been sterile filtered into another syringe. The two syringes were coupled, the contents mixed together for 30 cycles, and the contents injected subcutaneously into prostate cancer patients who had been orchiectomized. Samples of serum were collected over 28 days and analyzed for leuprolide concentration using a validated RTA method. The data given in Table 4 show an initial burst of drug followed by fairly constant levels over 28 days. When these data are compared to those for Lupron® Depot published in the literature, the values are quite similar, and it is expected that both products will provide the same efficacy in prostate cancer patients.

TABLE 4

Serum Leuprolide Data in Humans

| | Serum Leuprolide Levels, ng/mL | |
|---|---|---|
| Time, Days | ATRIGEL ® | Lupron ®[1] |
| 0.167 | 25.26 | 20 |
| 14 | 0.28 | — |
| 17 | — | 0.8 |
| 21 | 0.37 | — |
| 28 | 0.42 | 0.36 |

[1]Sharifi

Example 5

The ATRIGEL® leuprolide product described in Example 4 was injected subcutaneously (s.c.) into prostate cancer patients in a pivotal clinical trial. Every 28 days, the patients were given another injection of the product until 6 injections had been received. Samples of serum were collected at various times and analyzed for testosterone concentration by a validated RIA method. The values given in Table 5 show that the serum testosterone concentrations reached castrate values of 50 ng/dL (0.5 ng/mL) at 21 days. The testosterone concentrations then declined to 7.77 ng/dL at day 56 and remained at this level throughout the remainder of the study. A comparison of the testosterone concentrations to the published values obtained with Lupron® Depot as given in Table 5 shows the ATRIGEL® leuprolide product to be more effective as it produces a lower testosterone level in humans.

TABLE 5

Serum Testosterone Data in Humans

| | Serum Testosterone Levels, ng/dL | |
|---|---|---|
| Time, Days | ATRIGEL ®[1] | Lupron ®[2] |
| 0 | 397.8 | 370.6 |
| 4 | 523.0 | 552.7 |
| 21 | 49.37 | 33.8 |
| 28 | 23.02 | 17.0 |
| 56 | 7.77 | ≤15.0 |
| 84 | 7.77 | ≤15.0 |
| 112 | 6.93 | ≤15.0 |
| 140 | 7.41 | ≤15.0 |
| 168 | 7.58 | ≤15.0 |

[1]= 36 patients
[2]= 56 patients (Sharifi)

Example 6

Poly(DL-lactide-co-glycolide) with a molar ratio of lactide to glycolide of 75/25 (Birmingham Polymer, Inc.) was dissolved in NMP to give a solution with 45% by weight polymer. This solution was filled into 3.0 cc polyproylene syringes with a male luer lock fitting and terminally sterilized by exposure to gamma irradiation at 23.2-24.6 kilograys. The polymer molecular weight after irradiation was 15,094 daltons. Leuprolide acetate was dissolved in water, sterile filtered through a 0.2 cm filter and filled into a polypropylene syringe with a male luer lock fitting. The aqueous solution was frozen and the water removed by vacuum to yield a lyophilized cake of leuprolide. The two syringes were connected together with a coupler immediately prior to use and the contents of the two syringes mixed by moving the material back and forth between the two syringes for 40 cycles to provide a formulation with 6% by weight of leuprolide acetate. The product was then pulled into the syringe with the male luer lock fitting and a one-half inch 20 gauge needle attached.

The formulation containing the leuprolide acetate was then injected subcutaneously into 5 male beagle dogs at a target dose of 25.6 µg/kg/day. The commercially available 3-month Lupron® Depot microspheres were injected intramuscularly into 5 male beagle dogs at the same target dosage. The actual dosages were 31.4 µg/kg/day for the ATRIGEL® formulation with leuprolide and 25.3 µg/kg/day for the Lupron® Depot product. At baseline and on days 1, 2, 3, 4, 7, 14, 21, 28, 35, 49, 63, 71, 81, 91, 105, 120, 134, and 150, serum was collected from each of the dogs and analyzed for testosterone by RIA and for leuprolide concentration by LC/MS/MS.

The data showed that the serum leuprolide levels were actually higher for the ATRIGEL® formulation compared to the Lupron® Depot product over the first 30 days, but then declined to the same levels as the Lupron® Depot product over the next 120 days (FIG. 1). However, the testosterone levels were comparable for the two product during the 70 days, but then the Lupron® Depot product failed to maintain human castration levels of testosterone. This result was surprising based upon the comparable leuprolide levels of the two products over the later time points.

Example 7

The same polymer formulation as described in Example 6 was prepared and filled into 1.25 cc polypropylene syringes with a female luer lock fitting at a volume of 440 mL. The product was terminally sterilized by exposure to gamma irradiation at 23-25 kilograys. The molecular weight of the polymer after irradiation was 14,800 daltons. Leuprolide acetate was dissolved in water, sterile filtered using a 0.2 cm filter, and filled into a 1.00 cc polypropylene syringe with a male luer lock fitting. The aqueous solution was frozen and the water removed by vacuum to give a 28.2 mg lyophilized cake of leuprolide acetate. Immediately before use, the two syringes were coupled together and the contents mixed by moving the materials back and forth between the two syringes for 40 cycles to provide a homogeneous mixture with 6% by weight leuprolide acetate. The formulation was then pulled into the syringe with the male luer lock fitting, the syringes disconnected, and a one-half inch 20 gauge needle attached.

Figure 3:
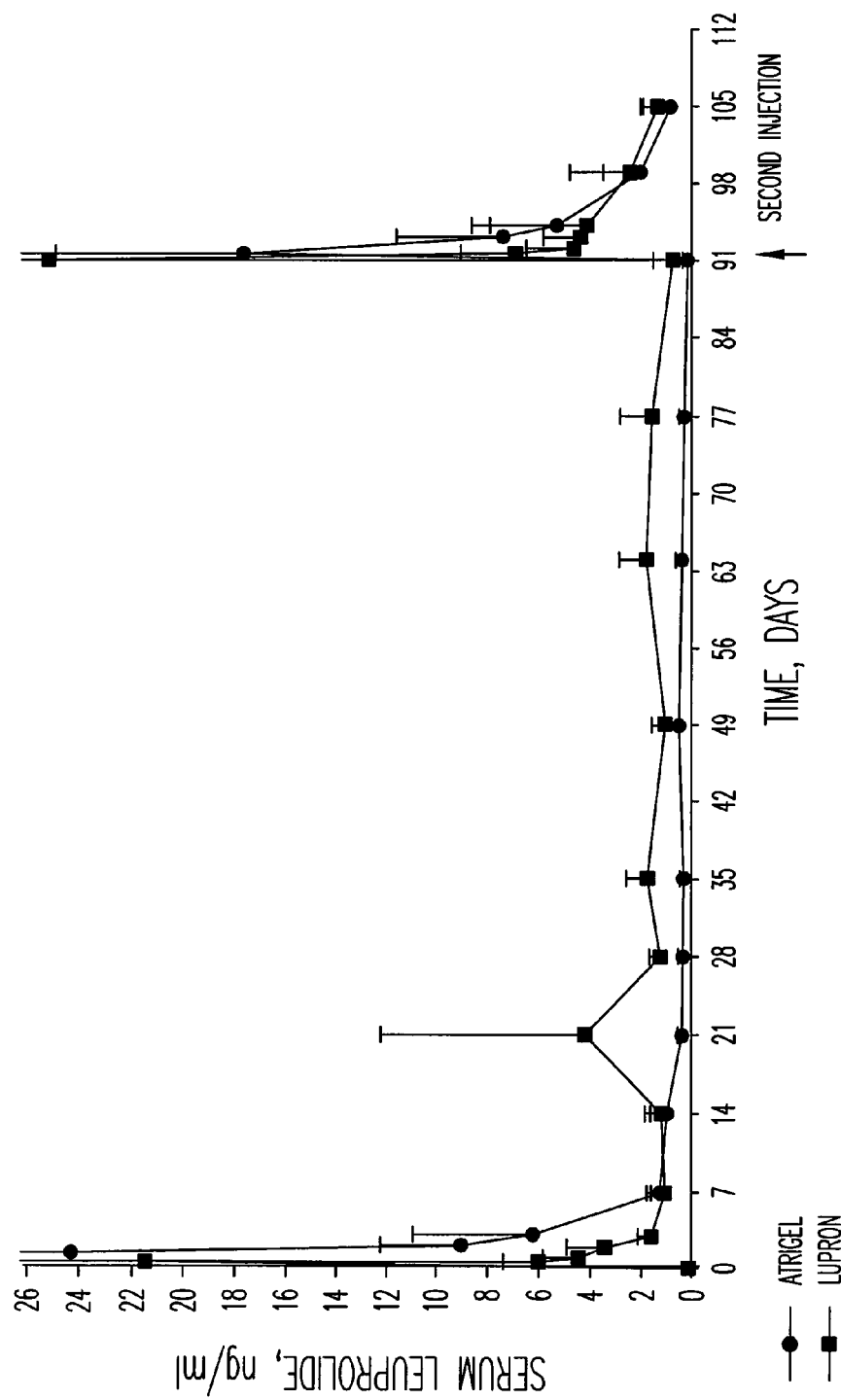
FIG. 3 illustrates serum leuprolide levels after ATRIGEL® and LUPRON® 90 day formulations administration in dogs (n=8), dosed at 22.5 mg LA.
Figure 4:
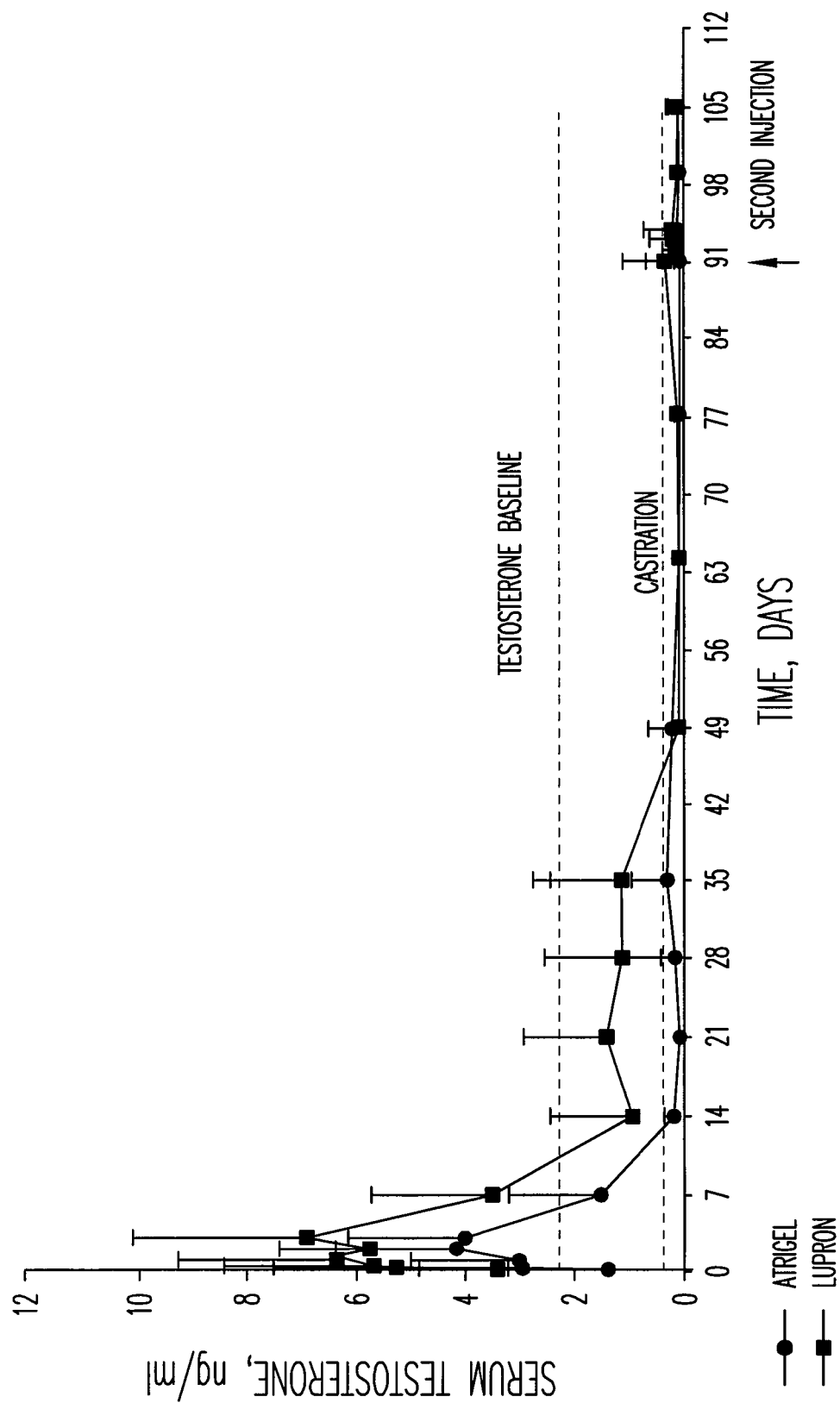
FIG. 4 illustrates serum testosterone levels after ATRIGEL® and LUPRON® 90 day formulations administration in dogs (n=8), dosed at 22.5 mg LA.

The formulation was injected subcutaneously into 8 male beagle dogs to give a total delivered dose of 22.5 mg of leuprolide acetate. The commercially available 3-month Lupron® Depot microspheres were injected intramuscularly into 8 male beagle dogs. At 6 and 12 hours, and on days 1, 2, 3, 7, 14, 21, 28, 35, 49, 64, 77, and 91 serum samples were collected for analysis of testosterone and leuprolide concentrations. On day 91, the animals were injected again with the formulations and serum collected at 6 and 12 hours on day 91 and again on days 92, 93, 94, 99, and 105. The mean serum leuprolide concentrations were much higher for the Lupron® Depot product than the ATRIGEL® formulation at the extended time points as shown in Table 6 and FIG. 3. However, the testosterone concentrations were actually lower for the ATRIGEL® formulation as shown in Table 7 and FIG. 4.

TABLE 6

Mean (SD) Serum Leuprolide Levels (ng/ml) in Dogs (n = 8) after ATRIGEL ® and LUPRON ® 3-Month Administration

| Time, day | Mean, LA (ATRIGEL) | Mean, LA (Lupron) |
|---|---|---|
| 0 | 0.1 | 0.1 |
| 0.25 | 221.38 | 21.5 |
| 0.5 | 54.13 | 5.99 |
| 1 | 24.29 | 4.43 |
| 2 | 9.01 | 3.43 |
| 3 | 6.23 | 1.61 |
| 7 | 1.25 | 1.08 |
| 14 | 0.99 | 1.16 |
| 21 | 0.35 | 4.16 |
| 28 | 0.31 | 1.24 |
| 35 | 0.27 | 1.73 |
| 49 | 0.45 | 1.04 |
| 64 | 0.34 | 1.78 |
| 77 | 0.29 | 1.59 |
| 91 | 0.17 | 0.78 |
| 91.25 | 254.88 | 25.15 |
| 91.5 | 84.74 | 6.85 |
| 92 | 17.61 | 4.63 |
| 93 | 7.32 | 4.36 |
| 94 | 5.27 | 4.11 |
| 99 | 2.04 | 2.48 |
| 105 | 0.85 | 1.35 |

TABLE 7

Mean (SD) Serum Testosterone Levels (ng/ml) in Dogs (n = 8) after ATRIGEL ® and LUPRON ® 3-Month Administration

| Time, day | Baseline, T | Mean T (ATRIGEL) | Mean T (Lupron) |
|---|---|---|---|
| 0 | 2.29 | 1.42 | 3.38 |
| 0.25 | 2.29 | 3.45 | 5.25 |
| 0.5 | 2.29 | 2.92 | 5.67 |
| 1 | 2.29 | 2.99 | 6.35 |
| 2 | 2.29 | 4.14 | 5.74 |

TABLE 7-continued

Mean (SD) Serum Testosterone Levels (ng/ml) in Dogs (n = 8) after ATRIGEL ® and LUPRON ® 3-Month Administration

| Time, day | Baseline, T | Mean T (ATRIGEL) | Mean T (Lupron) |
|---|---|---|---|
| 3 | 2.29 | 3.98 | 6.92 |
| 7 | 2.29 | 1.51 | 3.46 |
| 14 | 2.29 | 0.17 | 0.95 |
| 21 | 2.29 | 0.06 | 1.38 |
| 28 | 2.29 | 0.14 | 1.13 |
| 35 | 2.29 | 0.29 | 1.11 |
| 49 | 2.29 | 0.2 | 0.07 |
| 64 | 2.29 | 0.05 | 0.07 |
| 77 | 2.29 | 0.05 | 0.08 |
| 91 | 2.29 | 0.06 | 0.34 |
| 91.25 | 2.29 | 0.06 | 0.22 |
| 91.5 | 2.29 | 0.05 | 0.22 |
| 92 | 2.29 | 0.05 | 0.14 |
| 93 | 2.29 | 0.09 | 0.22 |
| 94 | 2.29 | 0.07 | 0.22 |
| 99 | 2.29 | 0.06 | 0.08 |
| 105 | 2.29 | 0.05 | 0.08 |

Example 8

Three polymer formulations containing 45% by weight of 75/25 poly(DL-lactide-co-glycolide) having different molecular weights were prepared and filled into 1.25 cc polypropylene syringes with female luer lock fittings at a volume of 440 mL. The syringes were terminally sterilized by exposure to gamma irradiation at 23-25 kilograys. The molecular weights of the three polymers after irradiation were 11,901, 13,308, and 21,268. These polymer solutions were combined with lyophilized leuprolide acetate in another syringe and injected subcutaneously in dogs at a dosage of 22.5 mg as described in Example 7. Serum samples were collected at baseline and days 1, 7, 14, 21, 28, 35, 42, 56, 70, 84, 98, 112, and 126. The serum was analyzed for testosterone concentration by RIA. The data showed that the two lower molecular weight polymer formulations failed to suppress the testosterone concentrations below castrate for the full 90 days whereas the polymer with the molecular weight of 21,268 was effective over the 3 months evaluated.

Example 9

Figure 5:
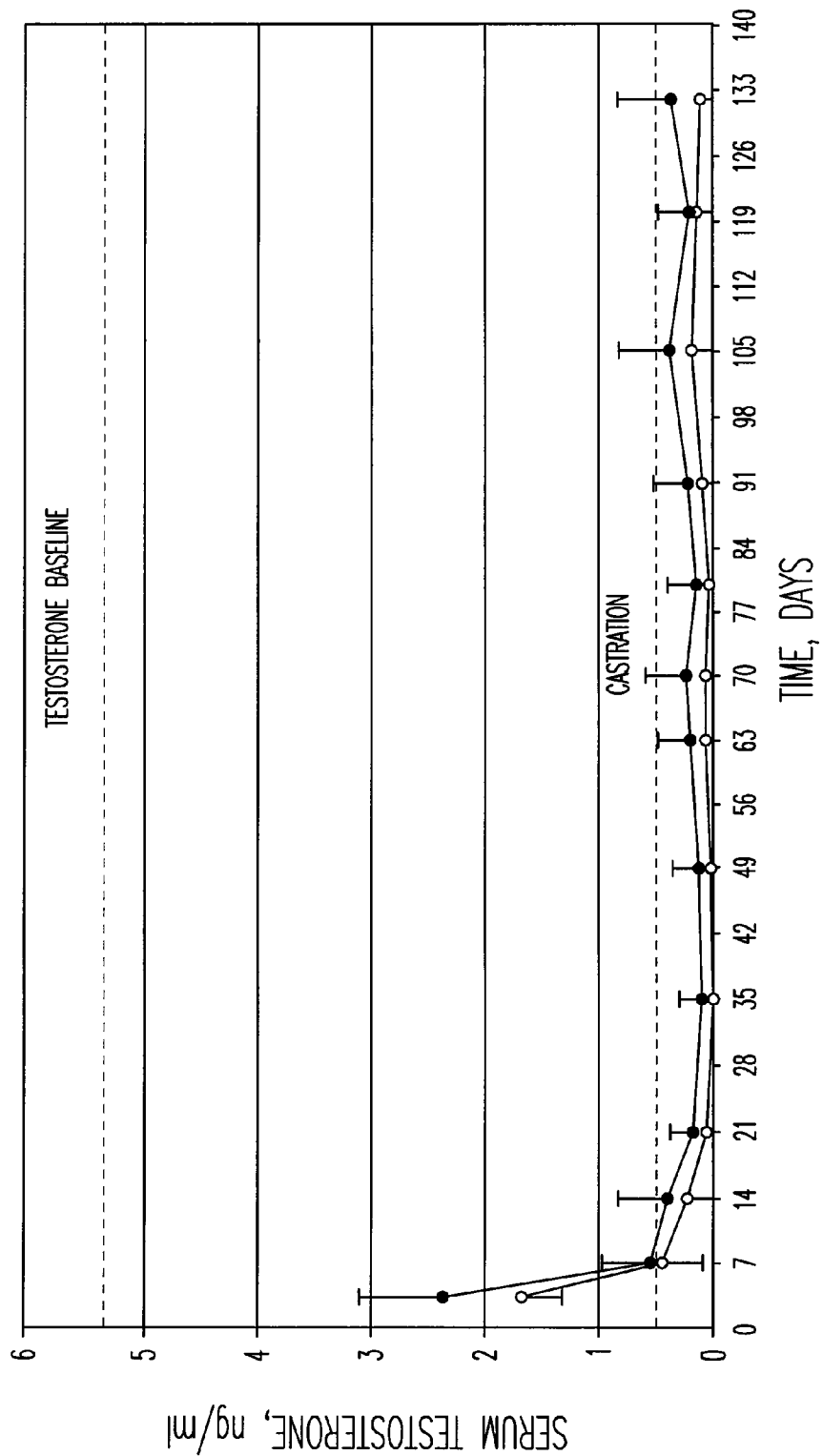
FIG. 5 illustrates serum testosterone levels in rats—4 month formulations, 14,860 daltons vs. 26,234 daltons.

Two polymer formulations containing 45% by weight 75/25 poly(DL-lactide-co-glycolide) having different molecular weights were prepared and filled into 1.25 cc polypropylene syringes. The syringes were terminally sterilized by exposure to gamma irradiation at 24-27 kilograys. The molecular weights of the two polymers after irradiation were 14,864 and 26,234 daltons. These polymer solutions were combined with lyophilized leuprolide acetate in another 1.25 cc polypropylene syringe and mixed back and forth for 40 cycles to produce a homogenous mixture with leuprolide acetate at 6% by weight. The contents were then pulled into one syringe, the syringes disconnected, and a one-half inch 20 gauge needle attached. The formulation with leuprolide acetate was then injected subcutaneously into 5 rats per group at a dosage of 100 µg/kg/day (12 mg/kg). At baseline and on days 3, 7, 14, 21, 35, 49, 63, 70, 80, 91, 105, 120, and 132 serum samples were collected from all of the animals and analyzed for testosterone concentration using an RIA method. The data shown in FIG. 5 indicate that both polymer molecular weight formulations were effective in suppressing testosterone below the human castrate level for 132 days.

What is claimed is:

1. A flowable composition suitable for use to form an in situ, single body controlled release implant, the composition consisting essentially of a non-aqueous, liquid solution of: (a) a biodegradable thermoplastic copolymer of lactide and glycolide that has a carboxy terminal group, that is at least substantially insoluble in aqueous medium or body fluid, and that has a weight average molecular weight of 15,000 to 45,000; (b) N-methyl-2-pyrrolidone; and (c) leuprolide acetate, wherein the copolymer is present in the composition at 30 wt % to 50 wt %; the N-methyl-2- pyrrolidone is present in the composition at 50 wt % to 70 wt % and the leuprolide acetate is present in the composition at 2 wt % to 8 wt %; and the composition is formulated for administration to a male patient about once per month to produce in situ the single body implant thereby reducing serum testosterone levels in the male patient.

2. A biodegradable implant formed in situ, in a male patient, by the steps comprising: (a) injecting 0.2 to 0.5 ml of the flowable composition of claim 1 within the body of the patient; and (b) allowing the N-methyl-2-pyrrolidone to dissipate to produce a solid, monolithic biodegradable implant of a microporous matrix of a core surrounded by a skin.

3. A method of reducing serum testosterone levels in a male human comprising injecting subcutaneously into the male human 0.2 ml to 0.5 ml of a flowable composition consisting essentially of a non-aqueous, liquid solution of: (a) a biodegradable thermoplastic copolymer of lactide and glycolide that has a carboxy terminal group, that is at least substantially insoluble in aqueous medium or body fluid, and that has a weight average molecular weight of 15,000 to 45,000; (b) N-methyl-2-pyrrolidone; and (c) leuprolide acetate in an amount sufficient to reduce LHRH levels in a human; wherein the copolymer is present in the composition at 30 wt % to 50 wt %; the N-methyl-2-pyrrolidone is present in the composition at 50 wt % to 70 wt % and the leuprolide acetate is present in the composition at 2 wt % to 8 wt %;

whereupon the flowable composition forms in situ a monolithic solid implant of a microporous matrix of a core surrounded by a skin within a body tissue of the male human by diffusion of the N-methyl-2-pyrrolidone into the body fluid of the male human and precipitation of the copolymer of lactide and glycolide.

* * * * *